(12) United States Patent
Rice

(10) Patent No.: US 8,778,487 B2
(45) Date of Patent: Jul. 15, 2014

(54) TAPE

(75) Inventor: Edward Claude Rice, Indianapolis, IN (US)

(73) Assignee: Rolls-Royce Corporation, Indianapolis, IN (US)

( * ) Notice: Subject to any disclaimer, the term of this patent is extended or adjusted under 35 U.S.C. 154(b) by 841 days.

(21) Appl. No.: 12/252,403

(22) Filed: Oct. 16, 2008

(65) Prior Publication Data

US 2010/0096183 A1  Apr. 22, 2010

(51) Int. Cl.
*B32B 5/02* (2006.01)
*B32B 9/00* (2006.01)
*B32B 7/12* (2006.01)

(52) U.S. Cl.
USPC ........... 428/221; 428/366; 428/343; 428/688; 428/297.4; 428/296.7; 428/364; 428/365; 428/368; 428/373; 428/402; 977/742; 977/750; 977/752; 977/753; 442/59; 442/172

(58) Field of Classification Search
USPC ............. 442/59, 172; 977/742, 750, 752, 753
See application file for complete search history.

(56) References Cited

U.S. PATENT DOCUMENTS

| | | | |
|---|---|---|---|
| 591,822 A | 10/1897 | Curtis | |
| 3,509,942 A | 5/1970 | Lindberg | |
| 3,979,949 A | 9/1976 | Smith | |
| 4,484,132 A | 11/1984 | Crites | |
| 4,503,710 A | 3/1985 | Oertle et al. | |
| 4,591,511 A | 5/1986 | Peebles, Jr. | |
| 4,641,539 A | 2/1987 | Vilimek | |
| 4,759,812 A | 7/1988 | Miller | |
| 4,961,977 A * | 10/1990 | Archer et al. ............. | 428/36.3 |
| 5,065,630 A | 11/1991 | Hadcock et al. | |
| 5,131,812 A | 7/1992 | Boyd et al. | |
| 5,518,565 A | 5/1996 | Castellucci et al. | |
| 5,638,165 A | 6/1997 | Duke et al. | |
| 5,650,570 A | 7/1997 | Goto et al. | |
| 5,698,977 A | 12/1997 | Simpson et al. | |
| 5,705,006 A | 1/1998 | Roudebush et al. | |
| 5,958,166 A | 9/1999 | Walters et al. | |
| 6,206,067 B1 | 3/2001 | Kociemba et al. | |
| 6,355,203 B1 | 3/2002 | Charmes et al. | |

(Continued)

FOREIGN PATENT DOCUMENTS

| | | |
|---|---|---|
| EP | 1775445 A2 | 4/2007 |
| GB | 1328167 | 8/1973 |

(Continued)

OTHER PUBLICATIONS

Ni, Qing-Qing; Shape memory effect and mechanical properties of carbon nanotube/shape memory polymer nanocomposites; Composite Structures, Elsevier Science LTD, GB, vol. 81, No. 2, Jun. 22, 2007, pp. 176-184, XP022131011, ISSN: 0263-8223 *p. 176-177*.

(Continued)

*Primary Examiner* — Matthew Matzek
(74) *Attorney, Agent, or Firm* — Krieg DeVault LLP

(57) ABSTRACT

A tape that can be used to detect cracks in a structure to which it is attached is disclosed herein. The tape includes a plurality of structural fibers. The tape also includes an electrically-insulating binder at least partially encapsulating the plurality of structural fibers. The tape also includes quantities of electrically conductive particles, each quantity of electrically conductive particles connected with one of the plurality of structural fibers.

13 Claims, 3 Drawing Sheets

(56) References Cited

U.S. PATENT DOCUMENTS

| | | |
|---|---|---|
| 6,419,187 B1 | 7/2002 | Buter et al. |
| 6,468,372 B2 | 10/2002 | Kociemba et al. |
| 6,656,299 B1 | 12/2003 | Grosskrueger et al. |
| 6,913,440 B2 | 7/2005 | Ciacci et al. |
| 7,141,990 B2 | 11/2006 | Bast et al. |
| 7,167,009 B2 | 1/2007 | van Schoor et al. |
| 7,216,428 B2 | 5/2007 | Memmen et al. |
| 7,225,681 B2 | 6/2007 | Stillman et al. |
| 7,278,830 B2 | 10/2007 | Vetters |
| 7,310,949 B2 | 12/2007 | Carper |
| 7,384,240 B2 | 6/2008 | McMillan et al. |
| 7,398,698 B2 | 7/2008 | Griess et al. |
| 2002/0180077 A1 | 12/2002 | Glatkowski et al. |
| 2003/0008125 A1 | 1/2003 | Delanoy et al. |
| 2003/0088980 A1 | 5/2003 | Arnold |
| 2005/0070185 A1* | 3/2005 | Schneider ............ 442/164 |
| 2007/0079507 A1 | 4/2007 | Cheng et al. |
| 2007/0128960 A1* | 6/2007 | Ghasemi Nejhad et al. ... 442/59 |
| 2007/0220748 A1 | 9/2007 | Dasilva et al. |

FOREIGN PATENT DOCUMENTS

| | | |
|---|---|---|
| GB | 2258732 A | 2/1993 |
| GB | 2430472 A | 3/2007 |
| JP | 2001082102 A | 3/2001 |
| WO | 2006046974 A2 | 5/2006 |
| WO | 2007015709 | 2/2007 |

OTHER PUBLICATIONS

EP Extended Search Report for EP09252425.5.

"Inexpensive Nanoglue Can Bond Nearly Anything Together;" Rensselaer Polytechnic Institute; Found at http://soenews.rpi.edu/update.do?artcenterkey=592.

Baker, Dr. A.A.; Repair Techniques for Composite Structures; (Jan. 1, 1990), Composite Materials in Aircraft Structures, Longman, New York, pp. 207-227, XP008103764, ISN: 9780582017122.

Yoshitake, et al.; Damage Evaluation for Composite Structures using Fiber Reinforced Composites as Self-Diagnosis Materials; SPIE, PO BOX 10 Bellingham WA 98227-0010, USA, 2004, XP040183195.

Thostenson et al.; Multifunctional Composites with Self-Sensing Capabilities: Carbon Nanotube-Based Networks; SPIE, PO BOX 10 Bellingham WA 98227-0010, USA, 2007, XP040238630.

Lazzaretto et al., Analytical and Neural Network Models for Gas Turbine Design and Off-Design Simulation, Int. J. Applied Thermodynamics, vol. 4, (No. 4), pp. 173-182, Dec. 2001.

Statutory Invention Registration, US H2057H, Jan. 7, 2003, Veers et al., Load Attenuating Passively Adaptive Wind Turbine Blade.

* cited by examiner

TAPE

BACKGROUND OF THE INVENTION

1. Field of the Invention

The invention relates to an apparatus and method operable to detect the presence of cracks in a structure.

2. Description of Related Prior Art

U.S. Pat. No. 4,484,132 shows a metal structure (P) covered with an insulating substrate (21) in FIG. 4. Electrically-conducting lines (22) are formed across the substrate (21). The lines (22) are a combination of electrically conductive particles suspended in a flowable material. The lines (22) are applied with a pen or syringe, shown in FIG. 10. After being applied to the substrate (21), the lines (22) cure and dry out. A second insulating layer (23) is applied over the lines (22). When the structure (P) cracks, the substrate (21) and lines (22) adjacent to the crack will also fracture, resulting in a change in voltage across at least one of the lines (22).

SUMMARY OF THE INVENTION

In summary, the invention is a tape that can be used to detect cracks in a structure to which it is attached. The tape includes a plurality of structural fibers. The tape also includes an electrically-insulating binder at least partially encapsulating the plurality of structural fibers. The tape also includes quantities of electrically conductive particles, each quantity of electrically conductive particles connected with one of the plurality of structural fibers.

BRIEF DESCRIPTION OF THE DRAWINGS

Advantages of the present invention will be readily appreciated as the same becomes better understood by reference to the following detailed description of an exemplary embodiment when considered in connection with the accompanying drawings wherein.

DETAILED DESCRIPTION OF THE EXEMPLARY EMBODIMENT

Figure 1:
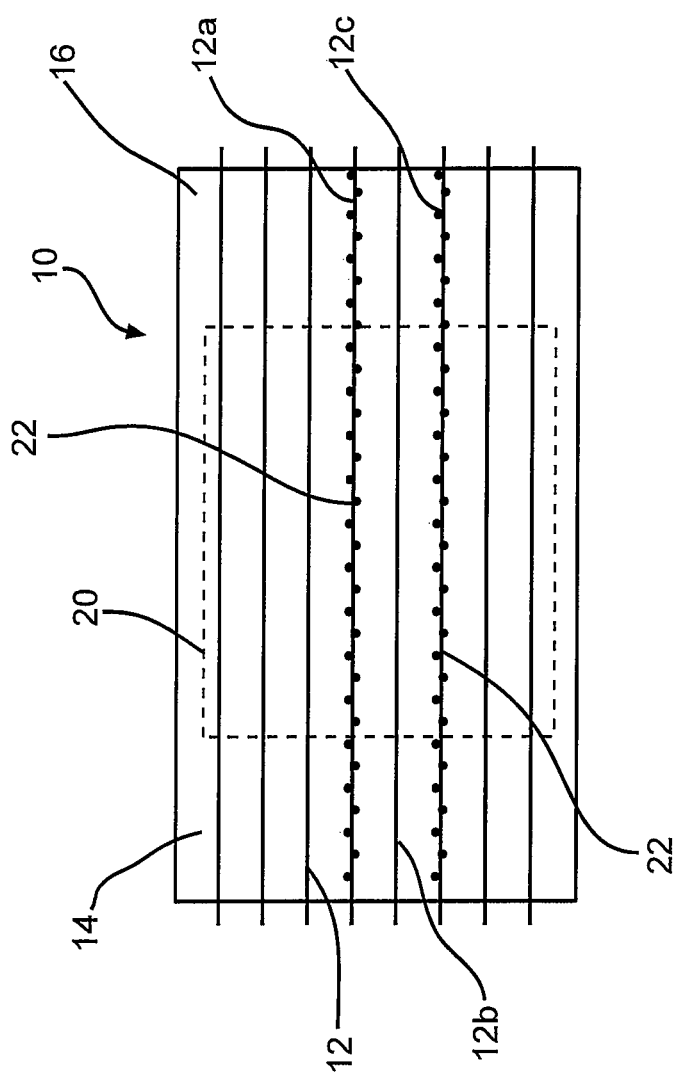
FIG. 1 is a top view of a parcel of tape according to an exemplary embodiment of the invention.
Figure 2:
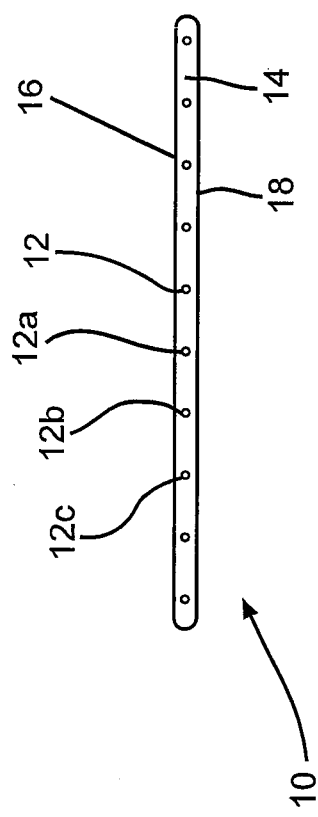
FIG. 2 is a right-hand view of the parcel of tape shown in FIG. 1.

Referring now to FIGS. 1 and 2, the exemplary embodiment of the invention is a tape 10 that can be used to detect cracks in a structure to which it is attached. The tape 10 and/or other embodiments of the invention may be applied in different operating environments and for different purposes. The exemplary tape 10 includes a plurality of structural fibers, such as fibers 12, 12a, 12b, 12c.

Each structural fiber 12, 12a, 12b, 12c can be a solid, elongate member with an appreciable length. The fibers 12, 12a, 12b, 12c can be of different lengths. In the exemplary embodiment of the invention, at least some of the fibers 12, 12a, 12b, 12c are boron fibers. However, alternative embodiments of the invention may include fibers formed from different materials. The multiple fibers 12, 12a, 12b, 12c of the tape 10 can also be fabricated from different materials relative to one another.

The fibers 12, 12a, 12b, 12c can be fabricated using different manufacturing processes, such as being spun, drawn, or woven. Some or all of the fibers 12, 12a, 12b, 12c can be flexible or rigid. One or more of the fibers 12, 12a, 12b, 12c can each be a single filament or can be a strand formed from a plurality of filaments interwoven with one another. Alternative embodiments of the invention can include a tape having a combination of single filament fibers and strand fibers.

The tape 10 also includes an electrically-insulating binder 14 at least partially encapsulating the plurality of structural fibers 12, 12a, 12b, 12c. The fibers 12, 12a, 12b, 12c can be substantially embedded in the binder 14, with only axially ends protruding as shown in FIG. 1. Alternatively, the tape 10 can be formed such that the fibers 12, 12a, 12b, 12c protrude out of a top surface 16 of binder 14 or a bottom surface 18 (referenced only in FIG. 2). Also, the tape 10 can be formed such that a "middle" portion of one or more of the fibers 12, 12a, 12b, 12c is exposed out of the binder 14. For example, the portions of the fibers 12, 12a, 12b, 12c within a box 20 shown in FIG. 1 can be exposed through the top surface 16 and covered by the bottom surface 18 shown in FIG. 2. The binder 14 can any material appropriate in view of the operating environment. In the exemplary embodiment of the invention, the binder 14 can at least partially include phthalonitrile.

The tape 10 also includes quantities of electrically conductive particles 22. Each quantity of electrically conductive particles 22 can be connected with one of the plurality of structural fibers 12a, 12c. The electrically conductive particles 22 can be various materials in particle form, with the particles ranging in size. In the exemplary embodiment of the invention, carbon nanotubes can be the electrically conductive particles 22. In alternative embodiments of the invention, the electrically conducting particles can be carbon (graphite), silver, gold, copper, platinum or even finely particulate alloy materials.

The electrically conductive particles 22 can be partially or fully embedded in the fibers 12a, 12c, or can be affixed to the outer surface of the fibers 12a, 12c. An amount of electrically conductive particles 22 can be connected with each fiber 12a, 12c until the conductivity across the respective fiber 12a, 12c reaches a suitable level. The fibers 12a, 12c themselves can be non-conductive or relatively poor conductors. The fibers 12a, 12c can be different from the electrically conductive particles 22 in at least one material property, such as conductivity or strength. For example, in one embodiment of the invention, the conductivity of copper may be desired so copper particles can be incorporated while the compressive properties of boron is desired so boron fibers are incorporated. The fibers 12a, 12c are larger than the electrically conductive particles 22.

FIG. 1 shows the fibers 12a and 12c each connected with a quantity of electrically conductive particles 22 and extending parallel to one another. The fibers 12a, 12c could be oriented differently in alternative embodiments of the invention. For example, the fibers 12a, 12c could be spokes of a hub and spoke pattern. Also, less than all of the structural fibers 12, 12a, 12b, 12c are connected with at least one of the quantities of electrically conductive particles 22 in the exemplary embodiment of the invention. However, in alternative embodiments of the invention, all of the fibers 12, 12a, 12b, 12c can be connected with at least one of the quantities of electrically conductive particles 22.

Figure 3:
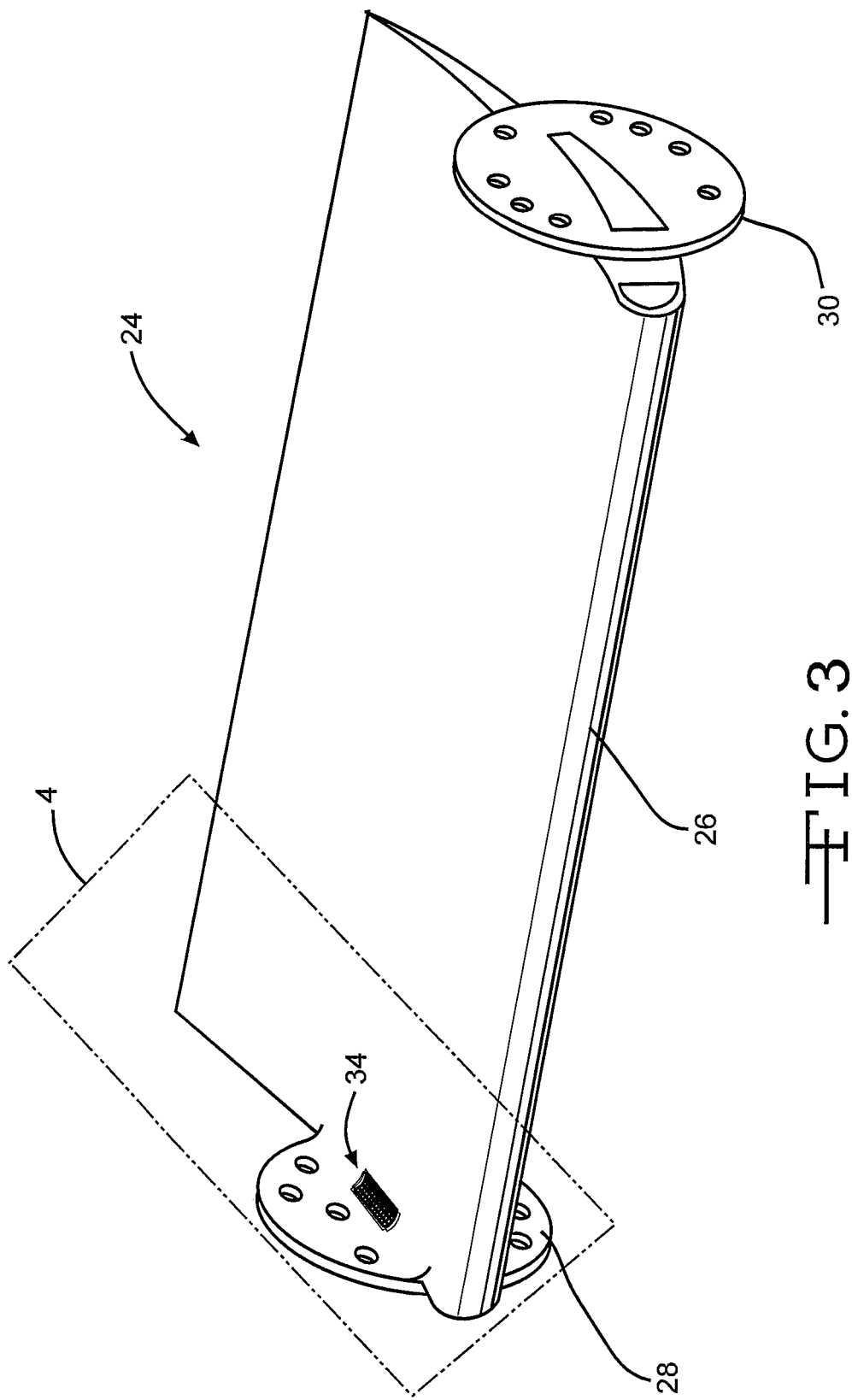
FIG. 3 is a perspective view of a structure according to another embodiment of the invention.
Figure 4:
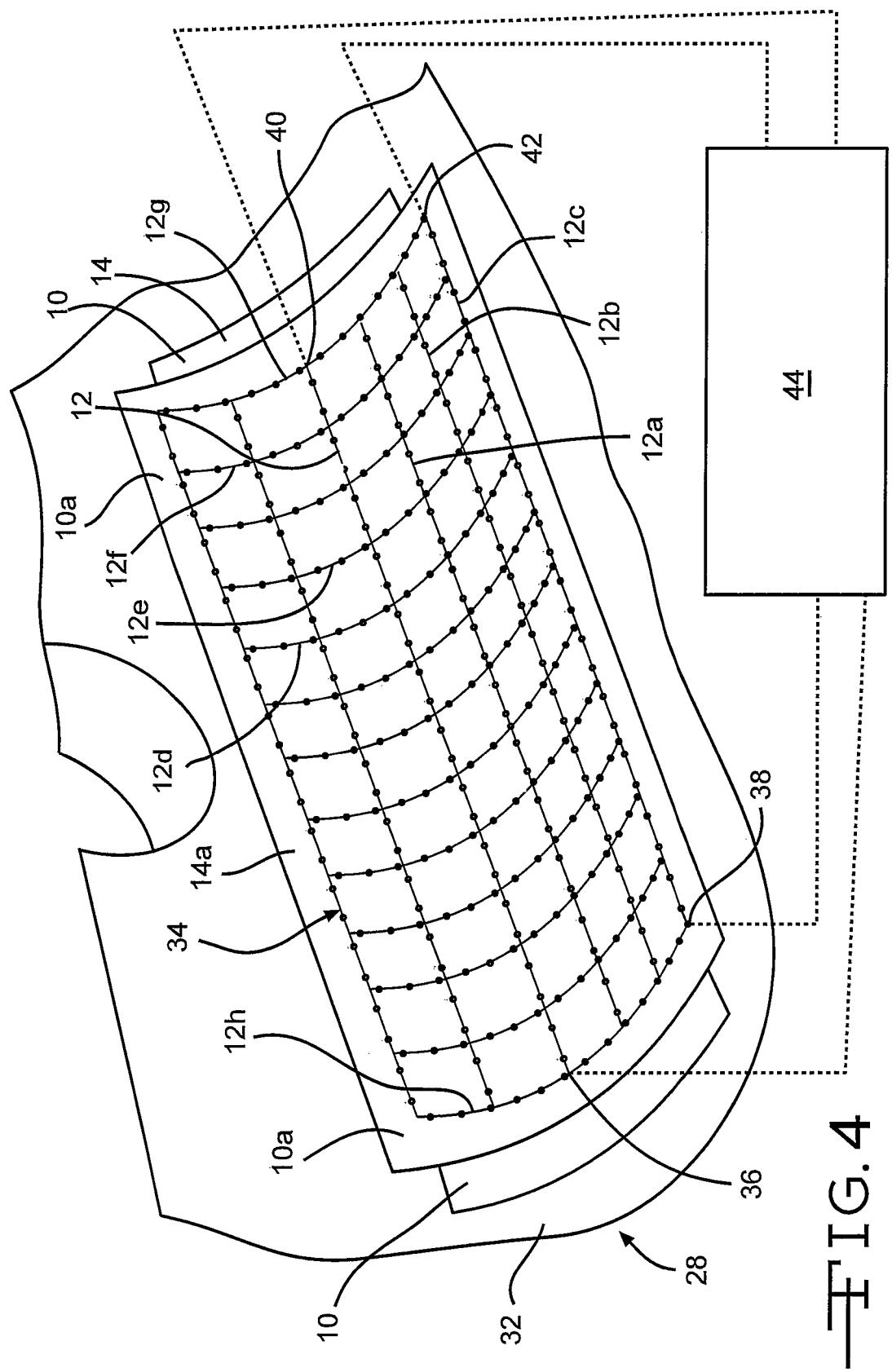
FIG. 4 is a magnified view of a portion of FIG. 3.

FIGS. 3 and 4 show an application of the exemplary embodiment of the invention. In FIG. 3, a vane assembly 24 for a vanebox can include a vane 26 shaped like an airfoil as well as first and second mounting end caps 28, 30. Generally, a vanebox is a structure that can direct a stream of air for propelling or positioning the aircraft, such as in short and/or vertical take-offs and landings. It is noted that the present invention is not limited to vaneboxes and that alternative embodiments of the invention can be practiced with structures used for other purposes.

The vane 26 and the end caps 28, 30 can be formed from any individual material or a composite of materials. In the exemplary embodiment of the invention, the vane 30 can include a structural foam core with a composite spar. The core and spar can be overlaid with layers of carbon fiber and resin as a skin. In alternative embodiments of the invention, the skin of the vane 36 could be the tape 10 shown in FIGS. 1 and 2 or a variation of the tape 10.

FIG. 4 is a magnified portion of end cap 28. The end cap 28 defines a body 32. A first parcel of tape 10 can be applied over a portion of the body 32 that is expected to experience relatively high loading during operation. The tape 10 can be applied to the body 32 with nanoglue or any other desired adhesive. The tape 10 can include a plurality of electrically conductive lines 12, 12a, 12b, 12c at least partially spaced from one another, an electrically-insulating binder 14 at least partially encapsulating the plurality of structural fibers 12, 12a, 12b, 12c, and quantities of carbon nanotubes 22, each quantity of carbon nanotubes 22 connected with one of the plurality of structural fibers 12, 12a, 12b, 12c. All of the structural fibers of the tape 10 in FIG. 4 can be connected with a quantity of carbon nanotubes 22.

A second parcel of tape 10a can be layered transversely over the first parcel of tape 10. The tape 10a can be partially applied to the body 32 and partially applied to the first parcel of tape 10 with nanoglue or any other desired adhesive. The tape 10a can include a plurality of electrically conductive lines 12d, 12e, 12f, 12g, 12h at least partially spaced from one another, an electrically-insulating binder 14a at least partially encapsulating the plurality of structural fibers 12d, 12e, 12f, 12g, 12h and quantities of carbon nanotubes 22, each quantity of carbon nanotubes 22 connected with one of the plurality of structural fibers 12d, 12e, 12f, 12g, 12h. All of the structural fibers of the tape 10a in FIG. 4 can be connected with a quantity of carbon nanotubes 22.

As described above with respect to FIG. 1, the tape parcels 10, 10a can be formed such that middle portions of the fibers 12-12h are exposed on one side. When the tape parcels 10, 10a are laid on top of one another, the exposed middle portions of the fibers 12-12h can contact one another and be operable to communicate electricity between one another. FIG. 4 shows at least one permissive difference from FIG. 1 in that the respective ends of the fibers 12-12h do not extend out of the respective binders 14, 14a.

As shown in FIG. 4, the parcels of tape 10, 10a can be applied on the body 32 such that the electrically conductive fibers or lines 12-12c of the first parcel of tape 10 are nonparallel to the electrically conductive fibers or lines 12d-12h of a second parcel of tape 10a. The lines 12-12h are made electrically conductive or have enhanced conductivity through the carbon nanotubes 22 or some other kind of electrically conductive particles. The electrically conductive lines 12d-12h therefore can form an electrical grid 34.

Electrical leads 36, 38, 40, 42 (shown schematically) can be connected to the grid 34 at various locations. A controller assembly 44 can direct current through the grid 34 through connections with the various electrical leads 36, 38, 40, 42 and monitor voltage levels at the each of the electrical leads 36, 38, 40, 42. Only four electrical leads 36, 38, 40, 42 are shown, however, the controller 44 can engage every intersection point of the grid 34 along the outer perimeter of the grid 34 in various embodiments of the invention.

If the body 32 cracks, at least one of the parcels of tape 10, 10a will crack, at least one of the conductive structural fibers 12-12h will sever, and voltage of at least one intersection point of the grid 34 along the outer perimeter of the grid 34 will change. The controller 44 can be operable to detect the location of the crack within the grid 34 based on changes in voltage at the various monitored points along the perimeter of the grid 34. One methodology for performing this analysis is set forth in U.S. Pat. No. 7,167,009, which is hereby incorporated by reference.

The first and second parcels of tape 10 and 10a individually and collectively increase the robustness of the body 32. In other words, the fibers 12-12h are bonded to the body 32 and thereby enhance the structural properties of the body 32. The material or combination of materials chosen to make the fibers 12-12h can be selected to increase the tensile strength of the body 32. When bonded to the body 32 at a location on the body 32 subject to tensile loads, these chosen fibers 12-12h can cause the tensile strength of the combined structure (body 32 and fibers 12-12h) to be greater than the tensile strength of the body 32 alone. Alternatively, the material or combination of materials chosen to make the fibers 12-12h can be selected to increase the compressive strength of the body 32. When bonded to the body 32 at a location on the body 32 subject to compressive loads, these chosen fibers 12-12h can cause the compressive strength of the combined structure (body 32 and fibers 12-12h) to be greater than the compressive strength of the body 32 alone. Generally, the fibers 12-12h can be selected such that the likelihood of cracking in the body 32 is reduced because of their attachment to the body 32.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A tape comprising:
a plurality of single layer structural fibers;
an electrically-insulating binder at least partially encapsulating said plurality of single layer structural fibers;
quantities of electrically conductive particles, each quantity of electrically conductive particles affixed to at least one of said plurality of single layer structural fibers;
wherein the plurality of single layer structural fibers along with the electrically-insulating binder and quantities of electrically conductive particles form a single layer tape, and the fibers located in the single layer tape are only the plurality of single layer structural fibers; and
wherein a portion of at least one of said quantities of electrical conductive particles is embedded in at least one of said plurality of single layer structural fibers.

2. The tape of claim 1 wherein less than all of said plurality of single layer structural fibers are affixed with at least one of said quantities of electrically conductive particles.

3. The tape of claim 1 wherein said quantities of electrically conductive particles include a first quantity of electrically conductive particles affixed to a first of said plurality of single layer structural fibers and a second quantity of electrically conductive particles affixed to a second of said plurality of single layer structural fibers, wherein said first and second single layer structural fibers are parallel to one another.

4. The tape of claim 1 wherein said plurality of structural fibers are electrically non-conductive.

5. The tape of claim 1 wherein each of said quantities of electrically conductive particles are further defined as carbon nanotubes.

6. The tape of claim 1 further comprising:
first and second electrical leads affixed to at least one of said plurality of single layer structural fibers being affixed with one of said quantities of electrically conductive particles, said first and second leads spaced from one another and operable to communicate a current through said quantity of electrically conductive particles.

7. The tape of claim 1 wherein said plurality of single layer structural fibers are further defined as boron fibers.

8. The tape of claim 1 wherein said binder is further defined as at least partially including phthalonitrile.

9. The tape of claim 1 further comprising:
an adhesive layer of nanoglue.

10. The tape of claim 1, wherein each quantity of electrically conductive particles affixed to at least one of said plurality of single layer structural fibers includes some of said quantity of electrically conductive particles embedded in at least one of said plurality of single layer structural fibers.

11. The tape of claim 1, wherein affixed to is defined to mean at least partially embedded therein.

12. A tape comprising:
a plurality of structural fibers;
an electrically-insulating binder at least partially encapsulating said plurality of structural fibers; and
quantities of electrically conductive particles, each quantity of electrically conductive particles embedded in at least one of said plurality of structural fibers.

13. The tape of claim 1 wherein all of said plurality of single layer structural fibers are affixed with at least one of said quantities of electrically conductive particles.

* * * * *